(12) United States Patent
Vaisnys et al.

(10) Patent No.: US 7,930,023 B2
(45) Date of Patent: Apr. 19, 2011

(54) AUTOMATIC EXTERNAL DEFIBRILLATOR WITH ACTIVE STATUS INDICATOR

(75) Inventors: Gintaras A. Vaisnys, Chicago, IL (US); Giovanni C. Meier, Madison, CT (US); Glenn W. Laub, Princeton, NJ (US)

(73) Assignee: Defibtech, LLC, Chicago, IL (US)

( * ) Notice: Subject to any disclaimer, the term of this patent is extended or adjusted under 35 U.S.C. 154(b) by 485 days.

(21) Appl. No.: 10/678,593

(22) Filed: Oct. 2, 2003

(65) Prior Publication Data

US 2004/0133244 A1    Jul. 8, 2004

Related U.S. Application Data

(63) Continuation-in-part of application No. 10/453,312, filed on Jun. 3, 2003, now Pat. No. 7,495,413, which is a continuation of application No. 09/960,859, filed on Sep. 21, 2001, now Pat. No. 6,577,102.

(51) Int. Cl.
*A61N 1/39* (2006.01)

(52) U.S. Cl. .......................................................... 607/5

(58) Field of Classification Search .................. 607/142, 607/29, 5, 145, 148, 149, 36, 4, 6, 129; 601/41, 601/15
See application file for complete search history.

(56) References Cited

U.S. PATENT DOCUMENTS

| | | | |
|---|---|---|---|
| 4,101,787 A | 7/1978 | Vail | |
| 4,590,943 A | 5/1986 | Paull et al. | |
| 4,610,254 A | 9/1986 | Morgan et al. | |
| 4,619,265 A | 10/1986 | Morgan et al. | |
| 5,224,870 A | 7/1993 | Weaver et al. | |
| 5,285,792 A | 2/1994 | Sjoquist et al. | |
| 5,350,317 A | 9/1994 | Weaver et al. | |
| 5,372,605 A | 12/1994 | Adams et al. | |
| 5,470,343 A * | 11/1995 | Fincke et al. | 607/5 |
| 5,483,165 A | 1/1996 | Cameron et al. | |
| 5,579,234 A | 11/1996 | Wiley et al. | |
| 5,591,213 A | 1/1997 | Morgan et al. | |
| 5,640,078 A | 6/1997 | Kou et al. | |
| 5,645,571 A * | 7/1997 | Olson et al. | 607/5 |
| 5,697,955 A | 12/1997 | Stolte | |
| 5,700,281 A | 12/1997 | Brewer et al. | |
| 5,741,305 A | 4/1998 | Vincent et al. | |
| 5,749,902 A | 5/1998 | Olson et al. | |

(Continued)

FOREIGN PATENT DOCUMENTS

JP    2001178021    6/2001

OTHER PUBLICATIONS

Machine translation of JP-2001178021.

(Continued)

*Primary Examiner* — Niketa I Patel
*Assistant Examiner* — Alyssa M Alter
(74) *Attorney, Agent, or Firm* — King & Spalding LLP

(57) ABSTRACT

An AED includes defibrillation circuitry housed within an enclosure, a first processor programmed to periodically test the operability of the defibrillation circuitry and a second processor in communication with the first processor. The AED further includes a visual indicator, such as a red/green LED, positioned at the exterior of the enclosure that is operatively connected to the second processor. The second processor is programmed to control the visual indicator in response to the periodic test results provided to it by the first processor.

33 Claims, 5 Drawing Sheets

U.S. PATENT DOCUMENTS

| | | | |
|---|---|---|---|
| 5,773,961 | A | 6/1998 | Cameron et al. |
| 5,792,190 | A * | 8/1998 | Olson et al. ............... 607/5 |
| 5,797,969 | A | 8/1998 | Olson et al. |
| 5,800,460 | A * | 9/1998 | Powers et al. ............ 607/5 |
| 5,817,151 | A | 10/1998 | Olson et al. |
| 5,846,264 | A | 12/1998 | Andersson et al. |
| D405,754 | S | 2/1999 | Barkley et al. |
| 5,868,790 | A | 2/1999 | Vincent et al. |
| 5,868,794 | A * | 2/1999 | Barkley et al. ........... 607/5 |
| 5,873,893 | A | 2/1999 | Sullivan et al. |
| 5,879,374 | A * | 3/1999 | Powers et al. ............ 607/5 |
| 5,889,388 | A | 3/1999 | Cameron et al. |
| 5,889,925 | A | 3/1999 | Tsurutani et al. |
| 5,891,049 | A | 4/1999 | Cyrus et al. |
| 5,897,576 | A | 4/1999 | Olson et al. |
| D409,752 | S | 5/1999 | Bishay et al. |
| 5,899,926 | A | 5/1999 | Ochs et al. |
| 5,904,707 | A | 5/1999 | Ochs et al. |
| 5,919,212 | A | 7/1999 | Olson et al. |
| 5,944,741 | A | 8/1999 | Ochs et al. |
| 5,951,485 | A | 9/1999 | Cyrus et al. |
| 5,955,956 | A | 9/1999 | Stendahl et al. |
| 5,964,786 | A | 10/1999 | Ochs et al. |
| 5,999,493 | A | 12/1999 | Olson |
| 6,016,059 | A | 1/2000 | Morgan |
| 6,021,352 | A | 2/2000 | Christopherson et al. |
| 6,073,085 | A | 6/2000 | Wiley et al. |
| 6,075,345 | A | 6/2000 | Lee |
| 6,075,369 | A | 6/2000 | Morgan |
| 6,185,458 | B1 | 2/2001 | Ochs et al. |
| 6,198,253 | B1 | 3/2001 | Kurle et al. |
| 6,366,809 | B1 * | 4/2002 | Olson et al. ............. 607/5 |
| 6,400,984 | B1 | 6/2002 | Medema |
| 6,546,288 | B1 | 4/2003 | Levine |
| 6,577,102 | B1 | 6/2003 | Vaisnys et al. |
| 6,650,942 | B2 | 11/2003 | Howard et al. |
| 6,955,864 | B1 * | 10/2005 | Vaisnys et al. ............ 429/121 |

OTHER PUBLICATIONS

Heartstream®. Fore Runner® Semi-Automatic Defibrillator User's Guide, pp. 6-9 and 50.
Hewlett Packard, 43110 A Defibrillator/Monitor Operating Guide, Eighth Edition, pp. 2, 5, 36-39, Aug. 1991.
Aligent Heartstream FR2, M3860A, M3861A, User's Guide, pp. 2-1-2-2, 2-4, 4-5, and B6.
Medtronic Physio-Control, Lifepack® 500 Automated External Defibrillator, Service Manual, pp. 3 of 12-4-12, 7 of 12-10 of 12, 12 of 12.
Medtronic Physio-Control, Lifepak® 500 Automated External Defibrillator Operating Instructions, pp. 2-5-2-6, 5-7-5-11, 5-16-5-17, Mar. 2001.
Survivalink FirstSave™ Operation and Service Manual, pp. 20, 29-31, 65, 70, 84 and 85, 2000.

* cited by examiner

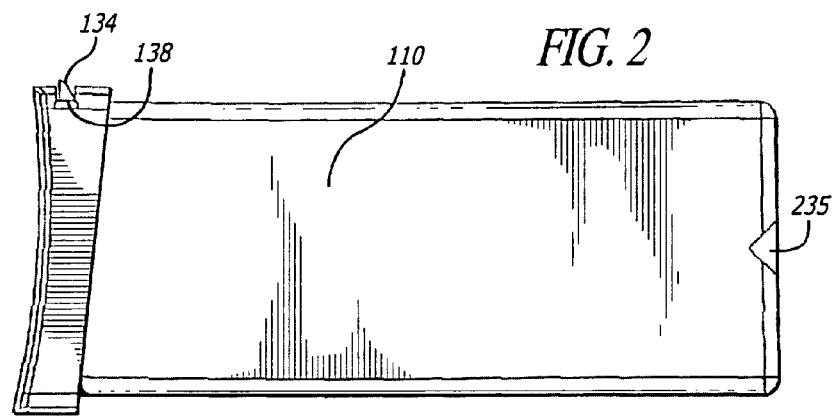
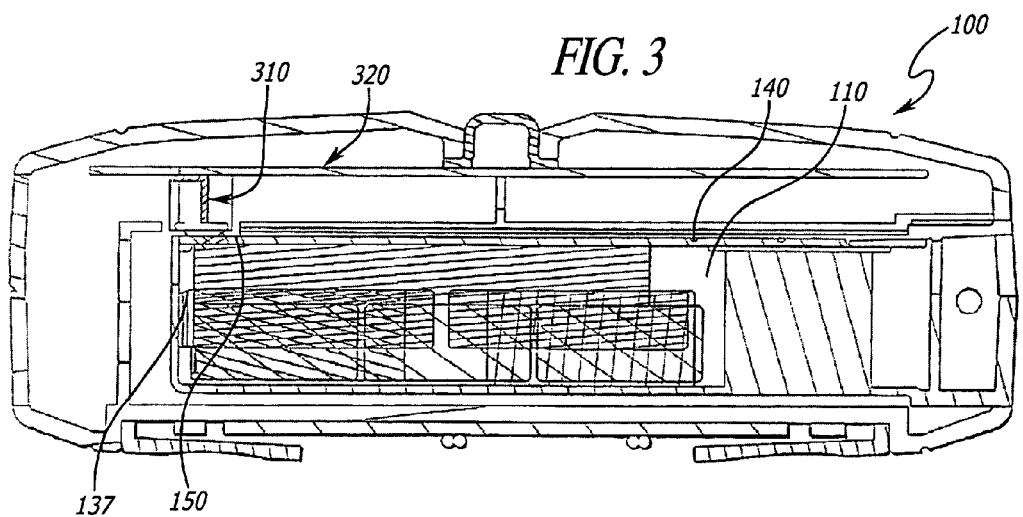
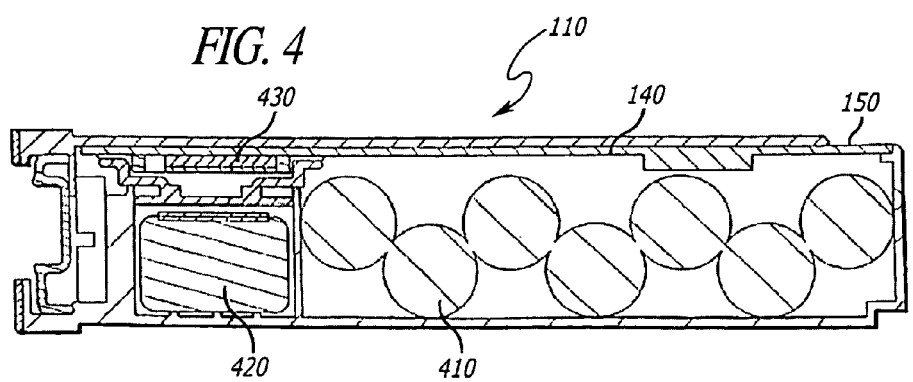

AUTOMATIC EXTERNAL DEFIBRILLATOR WITH ACTIVE STATUS INDICATOR

RELATED APPLICATIONS

This is a continuation-in-part of application Ser. No. 10/453,312, filed Jun. 3, 2003 now U.S. Pat. No. 7,495,413 which is a continuation of application Ser. No. 09/960,859, filed Sep. 21, 2001 now U.S. Pat. No. 6,577,102.

BACKGROUND OF THE INVENTION

1. Field of the Invention

This invention relates generally to external defibrillators, and more specifically to automatic external defibrillators (AED) having active status indicators that provide a continuous indication related to the operational readiness of the defibrillator. The invention further relates to AEDs having other operation indicators that provide indications related to the condition of the defibrillator during use.

2. Description of Related Art

Conventional AEDs perform periodic self-tests to determine the operational readiness of the defibrillator. Some defibrillators perform such self-tests automatically when they are turned on. Other defibrillators perform self-tests on a periodic basis regardless of the on/off state of the defibrillator. The results of these tests, however, may not be indicated until subsequent turn-on of the AED or may not be readily apparent to the user of the AED.

Hence, those skilled in the art have recognized a need for providing a continuous, active indication of the operational readiness of an external defibrillator regardless of the on/off state of the defibrillator. The need for additional indications of the condition of a defibrillator during use has also been recognized. The invention fulfills these needs and others.

SUMMARY OF THE INVENTION

Briefly, and in general terms, the invention is directed to an AED that provides a continuous, active indication of the operational readiness of the defibrillator. This active indication is provided by a visual indicator carried by the enclosure of the AED. The visual indicator may be a single LED capable of displaying different first and second colors, e.g., red and green. Alternatively the visual indicator may be two separate LEDs or may be a mechanical type indicator having different first and second positions, each having an associated color.

An AED incorporating aspects of the invention includes defibrillation circuitry housed within an enclosure, a first processor programmed to periodically test the operability of the defibrillation circuitry and a second processor in communication with the first processor. The AED further includes a visual indicator, as described above, positioned at the exterior of the enclosure that is operatively connected to the second processor. The second processor is programmed to control the visual indicator in response to the periodic test results provided to it by the first processor. Alternatively, the first and second processors may be combined into a single processor.

In one configuration, the second processor is programmed to 1) cause the indicator to continuously present a first color, e.g., green, when the defibrillator is on and the periodic test result is that the defibrillation circuitry is operating normally; 2) cause the indicator to intermittently present the first color when the defibrillator is off and the periodic test result is that the defibrillation circuitry is ready to operate normally; 3) cause the indicator to continuously present a second color, e.g., red, when the defibrillator is on and the periodic test result has detected an error in the defibrillation circuitry and 4) cause the indicator to intermittently present the second color when the defibrillator is off and the periodic test result has detected an error in the defibrillation circuitry.

In another aspect, the invention is directed to an AED that provides visual and/or audible indications of the condition of a defibrillator during use. These indications relate to the operation of the AED in conjunction with the electrode pad assembly used to monitor a patient's heart activity and administer defibrillation shocks.

An AED related to this aspect of the invention includes defibrillation circuitry housed within an enclosure and an electrode pad assembly adapted for electrical communication with the defibrillation circuitry at one end and a patient at the other end. The AED further includes a processor programmed to monitor the operation of the defibrillation circuitry and electrode pad assembly and a visual indicator positioned at the exterior of the enclosure and operatively connected to the processor. The AED may also include a speaker. The processor is programmed to control the visual indicator and/or speaker in response to the results of the operation monitoring.

These and other aspects and advantages of the invention will become apparent from the following detailed description and the accompanying drawings which illustrate by way of example the features of the invention.

BRIEF DESCRIPTION OF THE DRAWINGS

FIG. 2 illustrates a bottom view of the battery pack;

FIG. 3 illustrates a side sectional view of the AED including the battery pack;

FIG. 4 illustrates a side sectional view of the battery pack including first and second battery units;

DETAILED DESCRIPTION OF THE PREFERRED EMBODIMENTS

Figure 1A:
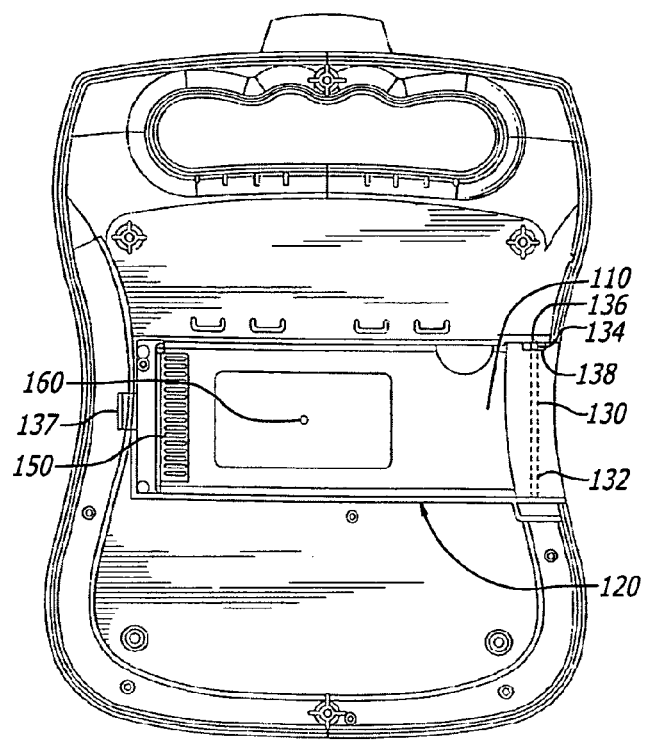
FIG. 1A illustrates a top sectional view of an AED with a battery pack installed.

FIG. 1A illustrates a top sectional view of the Semi-Automatic External Defibrillator ("AED") 100 that includes a battery system, for example battery pack 110. The AED 100 is a device to treat cardiac arrest that is capable of recognizing the presence or absence of ventricular fibrillation or rapid ventricular tachycardia or other shockable cardiac arrhythmias, and is capable of determining, without intervention by an operator, whether defibrillation should be performed. Upon determining that defibrillation should be performed, the AED automatically charges and requests delivery of electrical energy to electrodes that attach to a patient to deliver the energy to the patient's heart.

The battery pack 110 provides power to components such as electronics and a charger located in the AED 100. The charger charges a capacitor 564 (FIG. 5) of the AED 100 that provides the electrical energy to the electrodes attached to the patient. The AED 100 includes a generally rectangular shaped battery well 120 that is constructed and arranged to house the battery pack 110. The battery pack 110 is sized to slide in and out of the battery well 120 to releasably connect a power supply of the battery pack 110 to the AED 100.

Figure 1B:
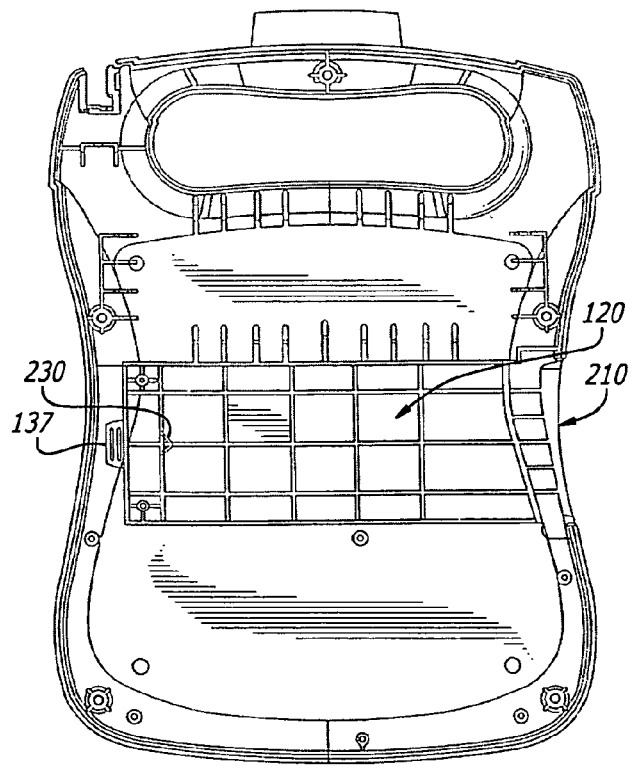
FIG. 1B illustrates a top sectional view of the AED with the battery pack removed.

FIG. 1B illustrates a top sectional view of the AED 100 and the battery well 120 with the battery pack 110 removed. An entrance 210 of the battery well 120 accommodates alignment of the battery pack 110 within the battery well 120.

FIG. 2 illustrates a bottom view of the battery pack 110. Referring to FIGS. 1B and 2, an opposite end of the battery well 120 includes a wedge-shaped feature 230 that corresponds to a wedge-shaped receptacle 235 located in the battery pack 110. When inserting the removable battery pack 110 to the AED 100, the battery pack 110 is guided along by the battery well 120 to the wedge-shaped feature 230. The battery pack 110 is aligned at the end of its travel by the wedge shaped feature 230 in the battery well 120 via the corresponding wedge shaped receptacle 235 in the battery pack 110.

Referring to FIG. 1A, to maintain the battery pack 110 in a connected position relative to the AED 100, the battery pack 110 includes a latch 130 that retains the battery pack 110 within the battery well 120 when the battery pack is fully inserted into the battery well 120. An end of the latch 130 connects with a spring 132 to bias the latch in a normally extended position. In the normally extended position, a latching end 134 of the latch 130 extends to enter a corresponding slot 136 located in the AED 100. The latch 130 is moveable in a plane parallel to the spring 132 to compress the spring 132 to release the latching end 134 from the slot 136. When the latching end 134 is released from the slot 136, an ejection spring 137 located on the AED 100 pushes on the battery pack 110 to eject the battery pack 110 from the battery well 120. The battery pack 110 includes a slot 138 from which the latch 130 extends. Even in a fully contracted position, the latch 130 extends past the slot 138.

Figure 5:
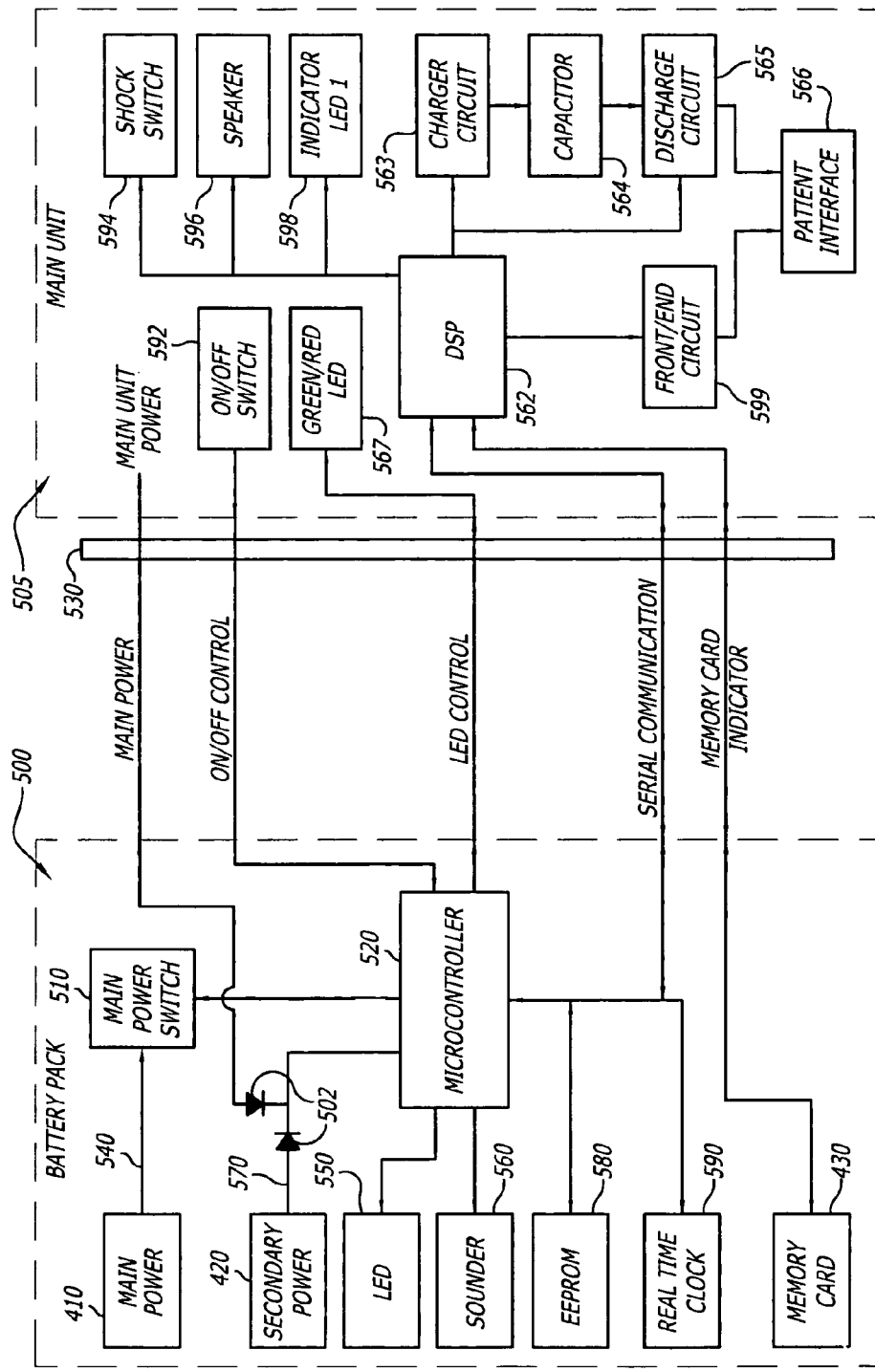
FIG. 5 illustrates a block diagram of one configuration of circuitry contained within the battery pack and the AED.

The battery pack 110 also includes a printed circuit board (PCB) 140 including exposed electrical terminals 150 to connect the printed circuit board 140 to electrical circuitry contained in the AED 100, as described in more detail below. The PCB 140 includes electrical components that connect to circuitry of the AED 100 when the battery pack 110 is installed in the AED 100. The battery pack 110 includes a window 160 that is located proximate to a visual indicator, such as light emitting diode (LED) 550 (FIG. 5). The window 160 allows an operator to view the LED 550 when the battery pack 110 is removed from the AED 100. Thus, the operator can determine a status of at least one of the AED 100 and the battery pack 110 independent of the battery pack 110 being connected to the AED 100. It should be appreciated that the AED 100 could also include a window located proximate to the battery pack window 160 so that an operator can view the LED 550 when the battery pack is inserted in the AED 100.

FIG. 3 illustrates a side sectional view of the AED 100 including the battery pack 110. The electrical terminals 150 of the PCB 140 contact a connector 310 located within the AED 100, to electrically connect the battery pack PCB 140 with an AED PCB 320.

FIG. 4 illustrates a side sectional view of the battery pack 110. The battery pack 110 includes a first power supply, such as battery unit 410. The battery unit 410 powers essential power needs of the AED during a main operating mode, for example when the AED is powered on. An essential power need includes, for example, the power necessary to charge the capacitor 564 to delivery energy to the patient. The battery unit 410 is preferably not being drained of power when the AED is powered off.

The battery unit 410 includes one or more battery cells, or other power supplies, that are electrically connected together. The power supply may include other forms of energy storage, for example based on chemical or kinetic principles, such as a flywheel storage device. The battery cells can include, for example, ⅔ A size batteries and/or C size batteries. The number of batteries used varies depending on a particular application but typically includes five or ten ⅔ A size batteries or four C size batteries. The five ⅔ A size batteries or four C size batteries are connected in series. Also, two sets connected in parallel of five ⅔ A batteries connected in series can be used for the battery unit 410. The battery unit 410 preferably powers electronics and a charger located in the AED 100.

The battery pack 110 also includes a secondary power supply, such as secondary battery 420. The secondary battery 420 powers at least a portion of at least one of the AED and the battery pack 110 in an alternate mode, such as when at least a portion of the AED is powered off. Those skilled in the art will appreciate that the secondary battery 420 could also be used to power the AED during other modes, such as a sleep mode or when the AED is powered on. The secondary battery 420 typically includes a single 9 Volt battery, but other power supplies could be used, such as other sized batteries or other forms of energy storage. In a preferred embodiment, the battery pack 110 accommodates replacement of the secondary battery 420. The secondary battery 420 can be sized smaller than the battery unit 410 and contain energy sufficient to power, for example, electric circuitry of the AED 100 and the battery PCB 140.

The secondary battery 420 can be used to power circuitry exclusive of a state of the battery unit 410 and without draining power from the battery unit. Diodes 502 (FIG. 5) electrically isolate the battery unit 410 from the secondary battery 420. Electric circuitry of the battery pack PCB 140 is described in more detail below with regard to FIG. 5. Such circuitry includes a socket to removably receive a memory device (FIG. 4), such as a memory card 430 or a multi-media card (MMC).

When the AED 100 is powered on and attached to the patient, the memory card 430 records the patient's electrocardiogram (ECG) signals, audio signals received from a microphone located on the AED 100, and other operational information such as results of an analysis done on the patient by software of the AED 100. The memory card 430 may also hold files that may be used to upgrade the software of the AED 100 or to provide user training mode software for the AED.

FIG. 5 shows a block diagram illustrating battery pack circuitry 500 contained with the battery pack 110, for example, on the battery pack PCB 140, and main unit circuitry 505. The circuitry 500 includes a main power switch 510. The main power switch 510 connects with a digital logic, such as micro-controller 520, that turns the main power switch 510 on and off and controls other circuitry 500 of the battery pack PCB 140. In addition to or in place of the micro-controller 520, the digital logic can also include a microprocessor, a programmable logic device (PLD), a gate array and a custom integrated circuit. Other digital logic could also be used such as a Programmable Interface Controller (PIC) manufactured by Microchip Technologies, located in Chandler, Ariz.

The micro-controller 520 connects with a main AED connector 530 that connects circuitry of the battery pack PCB 140 to circuitry of the AED 100. When the operator engages a power switch 592 located on the AED 100, the micro-controller 520 receives a signal from the main unit connector 530 indicating that the power switch has been engaged. Thereafter, the micro-controller 520 enables the main power switch 510 to provide an electrical power between the battery unit 410 of battery pack 110 and the electronics of the AED 100. The battery pack PCB 140 also includes a main battery connector 540 to connect the battery unit 410 to the main unit connector 530 and other circuitry of the battery pack PCB 140.

The micro-controller 520 also controls a visual indicator, such as LED 550 and an audio indicator, such as sounder 560 that are used to automatically communicate information to the operator. For example, when the AED 100 fails a self-test, the operator is notified by a chirping sound from the sounder 560. Moreover, the LED 550 blinks green to indicate that a status of components of the AED 100 is within an acceptable operating range. Those skilled in the art can appreciate the opposite could be true, i.e., that a blinking light indicates a fault condition. According to a preferred embodiment, if the LED 550 is not blinking an error exists, for example, in the circuitry 500, or the battery unit 410 or secondary battery 420 are depleted. The micro-controller 520 monitors a signal of a comparator connected to secondary battery 420 to monitor a status of the secondary battery 420, for example, to determine whether or not power of the secondary battery 420 is low or depleted.

Regarding the main unit circuitry 505, a digital signal processor (DSP) 562 processes instructions and data of the AED 100. The DSP 562 connects with a charger circuit 563 and discharger circuit 565 to control the charging and discharging of main unit capacitor 564. The capacitor charger 563 connects the battery unit 410 to the capacitor 564. The capacitor 564 connects to a discharge circuit 565 that connects to patient interface 566 to deliver shocks to the patient.

The micro-controller 520 also controls an active status indicator (ASI), which in one embodiment is a red and green LED 567 located on the AED 100. In an alternate embodiment the ASI may include two separate LEDs, a red LED and a green LED. The micro-controller 520 connects to the red and green LED 567, for example, via pins of the main unit connector 530. The micro-controller 520 causes the LED 567 to blink green when the AED 100 is operating properly and causes the LED 567 to blink red when components of the AED are not within the acceptable operating range, for example, a component of the AED 100 failed during a self-test procedure. If the LED 567 is not blinking when the battery pack 110 is installed into the AED 100, components of the AED 100 and the battery pack 110 should be checked. The operation of the AED self-test procedures and the ASI are described further below. The battery pack LED 550 is preferably disabled when the battery pack 110 is installed.

The secondary battery 420 powers the micro-controller 520, the LED 550 and the LED 567, which helps to maintain the integrity of the battery unit 410 that provides power to electronics and the capacitor charger located in the AED 100. A secondary battery connector 570 connects the secondary battery 420 to the circuitry of the battery pack PCB 140.

The battery pack circuitry 500 also includes an electrically erasable programmable read only memory (EEPROM) 580 connected to the micro-controller 520 and the main unit connector 530. The EEPROM 580 stores information that may be relevant to an owner, service person or operator of the AED 100. The EEPROM 580 stores information regarding, for example, the number of shocks the battery unit 410 has been used for, that the AED 100 has been activated, the date of manufacture of the battery pack 110 and status information regarding a status of components of the battery pack 110 and the AED 100. The DSP 562 of the AED 100 connects to a bus that connects to a real time clock (RTC) 590, the EEPROM 580 and the micro-controller 520. Typically once per power up of the AED 100, the DSP accesses the RTC 590 to set a main unit clock of the AED 100 that is located in the DSP.

The main unit circuitry 505 also includes a switch 592, such as an ON/OFF switch, that connects to the micro-controller 520 via the main unit connector 530. A shock switch 594 connects to the DSP 562 to allow an operator to administer a shock to the patient. A speaker 596 and indicator LEDs 598 connect to the DSP 562 to supply instructions or other information to the operator. Front end circuitry 599 connects between the DSP 562 and the patient interface 566 to process and/or provide the DSP 562 with information from the patient.

Figure 6:
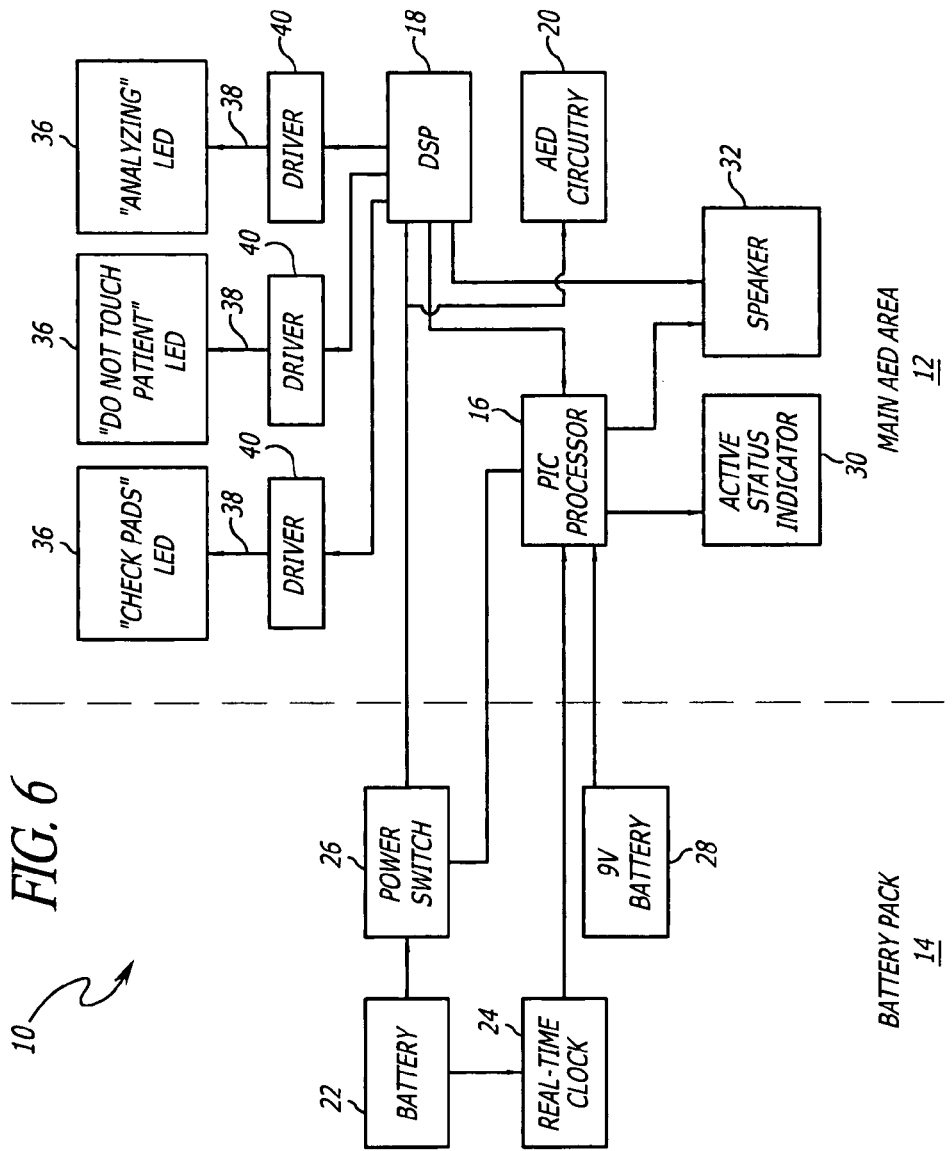
FIG. 6 illustrates a block diagram of another configuration of circuitry contained within the battery pack and the AED.

With reference to FIG. 6, in another configuration, the AED 10 consists of a main AED 12 and a removable battery pack 14. The main AED 12 includes a PIC processor 16, which is used to control power to the AED, a digital signal processor (DSP) 18, which is the main processor for the AED, and AED circuitry 20, which consists of the remainder of the AED circuitry. For a description of additional AED circuitry including the high-voltage circuitry used to generate and deliver defibrillation shock, see U.S. Pat. Nos. 5,607,454 and 5,645,571, the disclosures of which are hereby incorporated by reference. Alternate circuitry, within the purview of one of ordinary skill in the art, may be developed and employed. Thus, the scope of this invention is not intended to be limited to the circuitry described in the incorporated references.

The battery pack 14 is similar to that previously described with reference to FIG. 5, except that some components, including the micro-controller 520 (FIG. 5), i.e., the PIC processor, have been moved to the main AED 12 (FIG. 6). The battery pack 14 includes a battery 22, which contains multiple battery cells, a real-time clock 24, which keeps time and can generate an output signal on a regular basis, a power switch 26, which is used to couple the battery 22 to the main AED 12, and a 9V battery 20 used to provide power to the PIC processor 16 during the times that the power switch 26 is off.

The DSP 18 is configured to run a number of self-tests that check the operation of the DSP 18 and the AED circuitry 20 on a periodic basis to ensure that the AED is fully operational. When the main AED 12 is powered off, the PIC 16 is placed in a standby mode. The real-time clock 24, which is permanently powered from the battery 22, issues a periodic signal, typically every five seconds. This signal is routed to the PIC 16 and causes the PIC to "wake up" from standby mode. At that time, the PIC 16 flashes an ASI 30 to indicate AED status and also decrements a count of the number of times that it has been woken up since the count was last set. When this count reaches zero, indicating that approximately 24 hours have elapsed since the count was last set, the PIC 16 turns the power switch 26 on which applies power to the AED causing the DSP 18 to execute startup code.

During the startup sequence, the DSP 18 communicates with the PIC 16 to determine the reason for the power-up. Typical reasons are that the user pressed the on/off button on the AED or that the PIC 16 has initiated a self-test. If the reason is a self-test, the DSP 18 executes self-test code which tests a portion or a majority of the AED circuitry 20. The results of the self-test are communicated to the PIC 16 which then displays the AED status by blinking the ASI 30. The PIC may also be configured to sound a sounder, e.g., speaker 32. When the test is complete, the DSP 18 sets the wake-up counter to a value which will cause the PIC 16 to wake up the DSP 18 approximately 24 hours later and initiates main AED 12 shut-down. The PIC 16 then turns off power to the main AED 12 by switching off the power switch 26. In this manner the AED is tested on a regular basis.

A typical testing schedule is to do the following self-tests at the intervals indicated:

Every day: basic circuitry tests.

Once a week: basic circuitry tests, basic battery tests and basic high voltage circuit tests, Once a month: basic circuitry tests, additional battery tests and comprehensive high voltage circuit tests, including a partial-voltage internal shock.

Once every three months: basic circuitry tests, additional battery tests and comprehensive high voltage circuit tests, including a full-voltage internal shock.

Tests are performed in a "silent mode" where no user interface elements are exercised and the user is not able to tell that the tests are being executed. The user may also independently initiate a self-test by holding down the on/off button 42 (FIG. 7) on the AED for five seconds while turning the unit on. This will cause an extended self-test, similar in scope to the "once ever three months" test, to execute.

Figure 7:
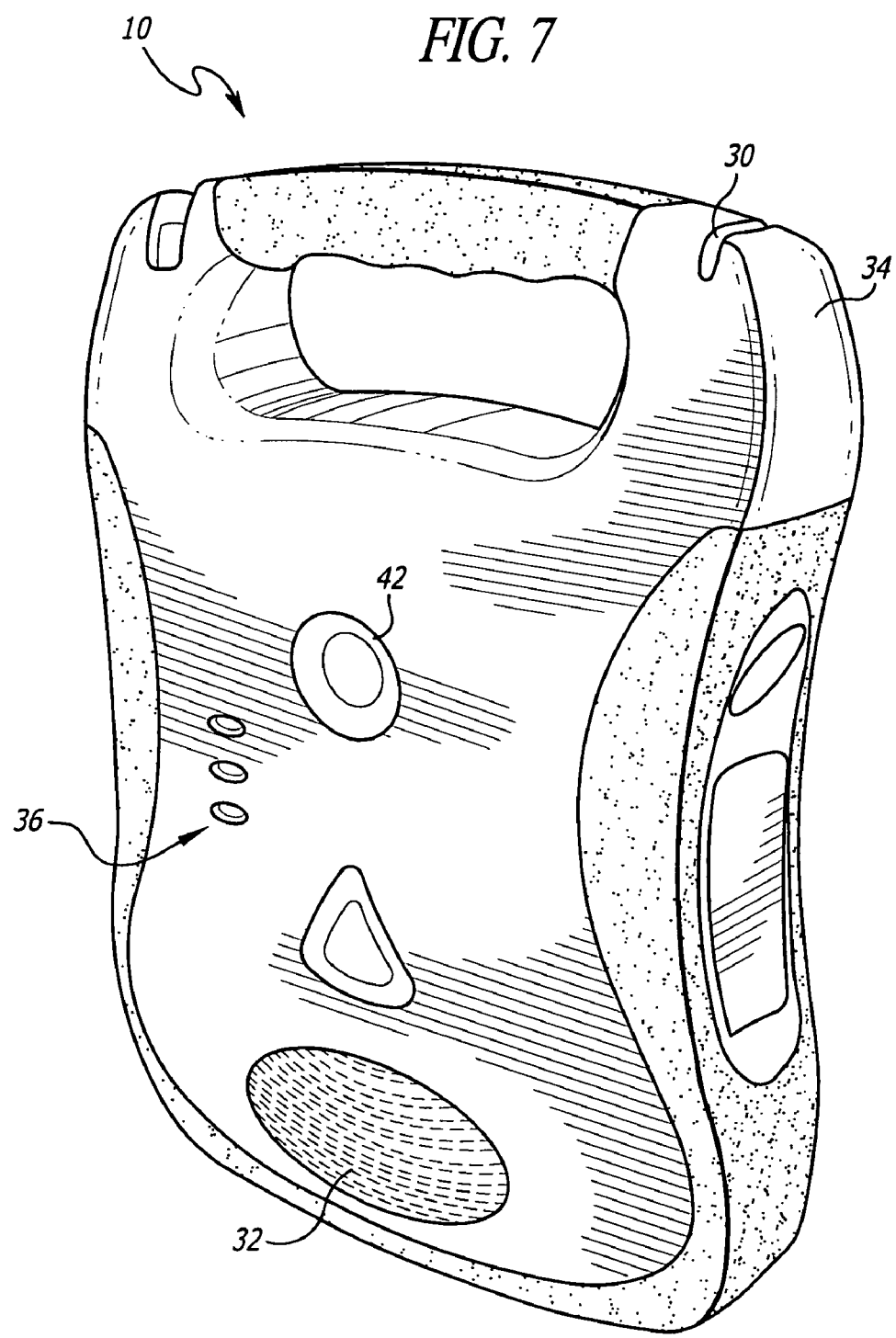
FIG. 7 is a perspective view of an AED including an active status indicator.

With reference to FIG. 7, the ASI 30 is located on the upper right side of the AED enclosure 34. The status indications provided by the ASI are as follows:

Steady-on green: the AED is on and operating normally.

Blinking green: the AED is off (in the stand-by mode) and is ready to operate normally.

Steady-On red: the AED is on and has detected an error.

Blinking red: the AED is off (in the stand-by mode) and the AED or battery pack needs servicing.

Off: battery pack not installed, AED defective, or the 9V battery is discharged.

Regarding the "blinking red" status, anytime the ASI 30 blinks red, the PIC 16 causes the speaker 32 to beep periodically to call attention to the AED. The ASI 30 is powered by the replaceable 9V battery 28 in the battery pack 14. If the 9V battery 28 has discharged, active status indication will not be available. In this case, the 9V battery 28 should be replaced. Once the 9V battery 28 has been replaced, the ASI 30 will once again flash a status indication. If the 9V battery 28 is depleted, the AED will still be fully functional and can be used in the on-state normally.

When the ASI 30 is blinking red, additional indications of the reasons for the blinking may be obtained by turning the AED on through the on/off button 42. These additional indications are provided by voice prompts programmed into the DSP 18 and output over the speaker 32. These voice prompts include:

"Power on self-test failed, error 'xxx'"—indicates that the AED has failed the power-on self-test and is non-operational and needs servicing. The code number xxx indicates the type of problem that the unit is experiencing.

"Battery pack self-test failed, error 'xxx'"—indicates that the AED's battery pack is non-operational and needs servicing. The code number xxx indicates the type of problem that the unit is experiencing.

"Error 'xxx', service required"—indicates that the AED has detected an internal error, is non-operational and needs servicing. The code number xxx indicates the type of problem that the unit is experiencing.

"Battery pack low"—indicates that the battery pack capacity is low and should be replaced soon. The AED will still be able to deliver at least a minimum of six defibrillation shocks the first time this message is spoken.

"Replace battery pack"—indicates that the battery pack is almost discharged and that the AED may not be able to deliver defibrillation shocks. The battery pack should be immediately replaced.

"Replace 9V battery"—indicates that the 9V battery in the battery pack needs to be replaced. The unit may not provide active status indication during standby mode in this condition, but the AED is still fully functional when turned on and may be used to treat patients. The 9V battery should be replaced as soon as possible.

As previously indicated with reference to FIG. 5, a speaker 596 and indicator LEDs 598 are connected to the DSP 562 to supply instructions or other information to the operator. With further reference to FIG. 7, in one configuration of the AED, these indicators 36 are located on the front panel of the enclosure 34 and include a red "check pads" LED, a red "do not touch patient" LED and a green "analyzing" LED.

As shown in FIG. 6, the indicator LEDs 36 are directly controlled by the DSP 18. Each LED 36 has a separate control line 38 and driver circuit 40. When the control line 38 is active the LED 36 is powered and lights up. The DSP 18 determines when to enable an LED 36 based on system state, i.e., connecting, motion, analyzing. The LED 36 can blink under software control by enabling and disabling the control line 38 at timed intervals.

The DSP 18 enables an LED 36 under the following conditions. The "check pads" LED blinks when the DSP 18 detects that the patient electrodes are not properly applied. The "do not touch patient" LED blinks when the DSP 18 detects patient motion and at times when the operator should stay clear of the patient. The "analyzing" LED blinks when the DSP 18 is analyzing the patient's ECG Signal. The process of determining conditions that activate these LEDs is described below within the context of additional indications provided by voice prompts.

In addition to the indications provided by the blinking LEDs 36, the DSP 18 is programmed to output voice prompts over the speaker 32 in association with certain conditions. Voice prompts associated with the "check pads" LED include "connect pads" and "check pads". "Connect pads" indicates that the DSP 18 has determined that the pads are not properly connected to the unit or not placed on the patient. This determination may be made by measuring the impedance across the pads. A high impedance is an indication that the pads are either not connected to the unit or not placed on the patient while a low impedance serves as an indication that the pads may be shorted together. What is considered "high" or "low" impedance is dependent on the electrical characteristics of electrode pad assembly and the internal defibrillator circuitry. "Check pads" indicates that the pads are making improper contact with the patient and that the impedance is out of range, i.e., either too high or too low, for proper ECG analysis and shock delivery.

Voice prompts associated with the "do not touch patient" LED include "do not touch patient", "stop motion" and "stop interference". "Do not touch patient" indicates that the DSP 18 is in the process of analyzing the patient's heart rhythm and that the operator should not touch the patient. The DSP 18 is programmed to analyze ECG signals once it has determined that the electrode pads are making good connection to the patient. The "do not touch patient" message is spoken at the beginning of the ECG analysis period and also if motion or interference has been detected. "Stop motion" indicates that the DSP 18 has detected motion in the patient, such as may occur during the administering of CPR. "Stop interference" indicates that the DSP 18 has detected interference on the ECG signal. In each of these cases, the DSP 18 monitors the characteristics of the ECG signals for indications of patient motion, e.g., an unexpected spike in the signal, and signal interference, e.g., a signal pattern containing noise or a signal of weak amplitude.

Voice prompts associated with the "analyzing" LED include "analyzing heart rhythm" and "analyzing interrupted". "Analyzing heart rhythm" indicates that the DSP 18 is actively analyzing the patient's ECG signal. The DSP 18 will continue analyzing until it has determined whether a rhythm is shockable or non-shockable or analyzing is interrupted for some reason. "Analyzing interrupted" indicates that the DSP 18 has determined that accurate ECG analysis is not possible and has ceased analyzing. The DSP 18 determines this condition by monitoring the ECG signal as previously described with respect to patient motion, signal interference and check pads. While the other LEDs may blink during this process, the "analyzing" LED will not be lit during this message.

While the invention has been described above by reference to various embodiments, it will be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, which are intended to define the scope of this invention.

What is claimed is:

1. An external defibrillator, comprising:
   a battery;
   defibrillation circuitry housed within an enclosure having an exterior, the defibrillation circuitry powered by the battery including
      a computer having programming to initiate and run recurring self-tests, which include at least some portion of the defibrillation circuitry and to perform a rescue, the self-tests occurring at intervals and capable of determining an operational status of the external defibrillator,
      a switch for a user to switch the external defibrillator from OFF to ON, wherein ON activates the defibrillation circuitry and its associated programming to perform a rescue, and OFF does not activate the defibrillation circuitry and its associated programming to perform a rescue but allows self tests to be conducted;
      an active status indicator comprising a light source that illuminates, the light source operated by the programming running on the computer, wherein the light source has a first illumination continually to indicate to an observer that the external defibrillator is OFF and that the most recent self-test has determined that the operational status is normal and thus the external defibrillator is ready to operate normally when turned ON and that presently maintenance is not required.

2. The defibrillator of claim 1 wherein the programming causes the active status indicator to present a second illumination in place of the first illumination when the defibrillator is ON and a self-test conducted as part of the rescue determines that the defibrillation circuitry is operational to indicate to the observer that the defibrillation circuitry is operating normally.

3. The defibrillator of claim 1 wherein the programming causes the active status indicator to present a third illumination in place of the first illumination when the defibrillator is ON and a self-test conducted as part of the rescue sequence determines that maintenance is required to indicate to the observer that maintenance is required.

4. The defibrillator of claim 1 wherein the programming causes the active status indicator to present a fourth illumination in place of the first illumination when the defibrillator is OFF and the most recent self-test has indicated that maintenance is required to indicate to the observer that maintenance is required.

5. The defibrillator of claim 1 wherein the first illumination includes blinking.

6. An external defibrillator, comprising:
   a battery pack;
   defibrillation circuitry housed within an enclosure having an exterior and connected to the battery pack, the defibrillation circuitry including
      a computer operating programming wherein the programming includes recurring self-tests of the defibrillation circuitry, the self-tests occurring at intervals,
      a switch for switching the external defibrillator from OFF to ON, the defibrillation circuitry when OFF being incapable of delivering a shock to a patient but able to perform recurring self-tests, and
      an active status indicator comprising a light source that illuminates, the light source operated by the programming running on the computer, wherein the light source is illuminated continually indicating that the external defibrillator is OFF and that the most recent self-test has determined that the external defibrillator is ready to operate normally if switched ON.

7. The external defibrillator of claim 6 wherein the defibrillation circuitry and electrode pads comprise electrical circuitry defining a high impedance threshold and a low impedance threshold and wherein a processor measures the impedance across the electrode pads, measures the impedance to the high impedance threshold and the low impedance threshold, and activates a second indicator when the measured impedance is either below the low impedance threshold or above the high impedance threshold.

8. The external defibrillator of claim 7 wherein active status indicator comprises a LED and the processor activates the LED by causing the LED to blink.

9. The external defibrillator of claim 8 wherein active status indicator further comprises a visual message display related to the operation being monitored.

10. The external defibrillator of claim 9 wherein the visual message display relates to a direction to check the electrode pads.

11. The external defibrillator of claim 7 further comprising a speaker, wherein the processor is further programmed to output an auditory message through the speaker related to the operation being monitored.

12. The external defibrillator of claim 11 wherein the auditory message relates to a direction to connect the electrode pads.

13. The external defibrillator of claim 6 wherein the defibrillation circuitry and electrode pads comprise electrical circuitry defining an impedance range proper for ECG analysis and shock delivery and wherein a processor is programmed to measure the impedance across the electrode pads, compare the impedance to the impedance range, and activate a second indicator when the measured impedance is outside the impedance range.

14. The external defibrillator of claim 13 wherein the active status indicator comprises a LED and the processor activates the LED by causing the LED to blink.

15. The external defibrillator of claim 14 wherein the active status indicator further comprises a visual message display related to the operation being monitored.

16. The external defibrillator of claim 15 wherein the visual message display relates to a direction to check the electrode pads.

17. The external defibrillator of claim 13 further comprising a speaker, wherein the processor is further programmed to output an auditory message through the speaker related to the operation being monitored.

18. The external defibrillator of claim 17 wherein the auditory message relates to a direction to check the electrode pads.

19. The external defibrillator of claim 6 wherein a processor is programmed to analyze ECG signals based on electrical signals received through the electrode pads; monitor the ECG signals for spikes, noise, and weak amplitude; and activate the active status indicator under any one of the following conditions: ECG signals being analyzed, spike detected, or noise or weak amplitude detected.

20. The external defibrillator of claim 19 wherein the active status indicator comprises a LED and the processor activates the LED by causing the LED to blink.

21. The external defibrillator of claim 20 wherein the active status indicator further comprises a visual message display related to the operation being monitored.

22. The external defibrillator of claim 21 wherein the visual message display relates to a direction to not to touch the patient.

23. The external defibrillator of claim 19 further comprising a speaker, wherein the processor is further programmed to output an auditory message through the speaker related to the condition.

24. The external defibrillator of claim 23 wherein the condition comprises ECG signals being analyzed and the auditory message relates to a direction to not to touch the patient.

25. The external defibrillator of claim 23 wherein the condition comprises a spike detected and the auditory message relates to a direction to stop motion.

26. The external defibrillator of claim 23 wherein the condition comprises noise or weak amplitude detected and the auditory message relates to a direction to stop interference.

27. The external defibrillator of claim 6 wherein a processor is programmed to analyze ECG signals based on electrical signals received through electrode pads and to activate the active status indicator during signal analysis.

28. The external defibrillator of claim 27 wherein the active status indicator comprises a LED and the processor activates the LED by causing the LED to blink.

29. The external defibrillator of claim 28 wherein the active status indicator further comprises a visual message display related to the operation being monitored.

30. The external defibrillator of claim 29 wherein the visual message display relates to analyzing heart rhythm.

31. The external defibrillator of claim 27 further comprising a speaker, wherein:
the defibrillation circuitry and the electrode pads comprise electrical circuitry defining an impedance range proper for ECG analysis and shock delivery, and
the processor is programmed to:
output a first auditory message through the speaker when ECG signals are being analyzed;
measure the impedance across the electrode pads, compare the impedance to the impedance range, and output a second auditory message through the speaker when the measured impedance is outside the impedance range; and
monitor the ECG signals for spikes, noise, and weak amplitude and output a third auditory message through the speaker under either of the following conditions: spike detected or noise or weak amplitude detected.

32. The external defibrillator of claim 31 wherein the first auditory message relates to the act of analyzing heart rhythm.

33. The external defibrillator of claim 31 wherein the second and third auditory messages relate to the interruption of heart rhythm analysis.

* * * * *